United States Patent
Oz

(10) Patent No.: US 8,452,594 B2
(45) Date of Patent: May 28, 2013

(54) METHOD AND SYSTEM FOR PROCESSING DICTATED INFORMATION

(75) Inventor: Mehmet Mert Oz, Vienna (AT)

(73) Assignee: Nuance Communications Austria GmbH, Vienna (AT)

( * ) Notice: Subject to any disclaimer, the term of this patent is extended or adjusted under 35 U.S.C. 154(b) by 1189 days.

(21) Appl. No.: 12/091,079

(22) PCT Filed: Oct. 16, 2006

(86) PCT No.: PCT/IB2006/053801
§ 371 (c)(1),
(2), (4) Date: Apr. 22, 2008

(87) PCT Pub. No.: WO2007/049183
PCT Pub. Date: May 3, 2007

(65) Prior Publication Data
US 2008/0235014 A1     Sep. 25, 2008

(30) Foreign Application Priority Data
Oct. 27, 2005   (EP) ..................................... 05110063

(51) Int. Cl.
*G10L 15/26*      (2006.01)
*G10L 21/00*      (2006.01)
*G06F 17/20*      (2006.01)

(52) U.S. Cl.
USPC ........... 704/235; 704/270; 715/224; 715/243; 715/273

(58) Field of Classification Search
None
See application file for complete search history.

(56) References Cited

U.S. PATENT DOCUMENTS 5,465,378 A * 11/1995 Duensing et al. ............. 715/233
5,617,855 A *  4/1997 Waletzky et al. ............. 600/586
6,766,297 B1 *  7/2004 Lamer et al. .................. 704/270
(Continued)

FOREIGN PATENT DOCUMENTS

CN    1263619 A    8/2000
CN    1609764 A    4/2005
(Continued)

OTHER PUBLICATIONS

Meisel, W.: "Speech Recognition and Medical Records"; Proceedings: Toward an Electronic Patient Record '96, 12th International Symposium on the Creation of Electronic Health Record System and Global Conference on Patient Cards, vol. 1, pp. 456-459, 1996.

(Continued)

*Primary Examiner* — Brian Albertalli
(74) *Attorney, Agent, or Firm* — Wolf, Greenfield & Sacks, P.C.

(57) ABSTRACT

A method and a system for processing dictated information into a dynamic form are disclosed. The method comprises presenting an image (3) belonging to an image category to a user, dictating a first section of speech associated with the image category, retrieving an electronic document having a previously defined document structure (4) associated with the first section of speech, thus associating the document structure (4) with the image (3), wherein the document structure comprises at least one text field, presenting at least a part of the electronic document having the document structure (4) on a presenting unit (5), dictating a second section of speech and processing the second section of speech in a speech recognition engine (6) into dictated text and associating the dictated text with the text field.

23 Claims, 1 Drawing Sheet

U.S. PATENT DOCUMENTS

Figure 1:
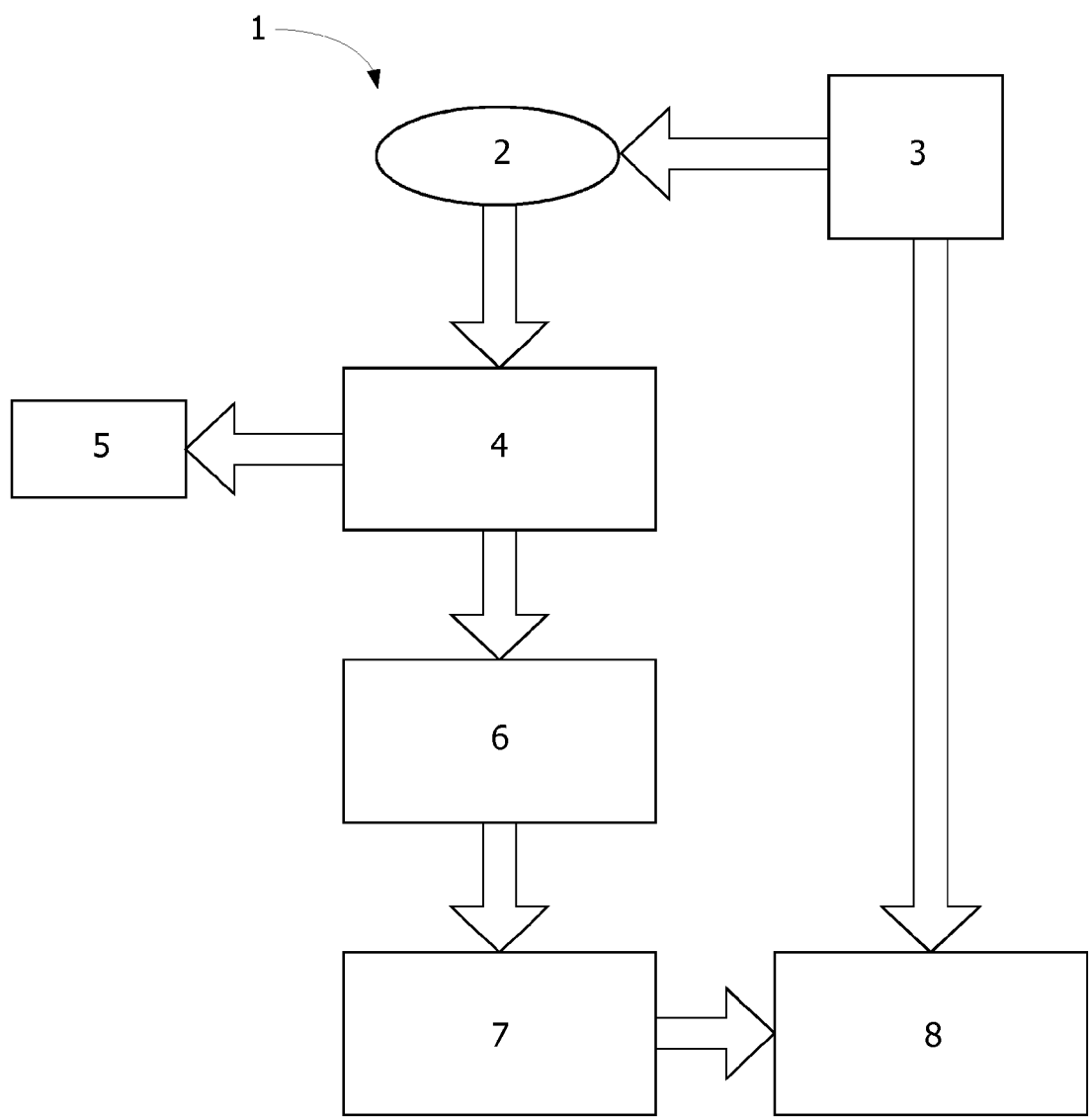

| | | | |
|---|---|---|---|
| 6,813,603 B1 * | 11/2004 | Groner et al. | 704/235 |
| 6,834,264 B2 * | 12/2004 | Lucas et al. | 704/235 |
| 7,370,275 B2 * | 5/2008 | Haluptzok et al. | 715/264 |
| 2002/0072896 A1 | 6/2002 | Roberge et al. | |
| 2003/0097253 A1 * | 5/2003 | Hoi | 704/9 |
| 2003/0115057 A1 | 6/2003 | Junqua et al. | |
| 2003/0154085 A1 * | 8/2003 | Kelley | 704/275 |
| 2004/0172245 A1 | 9/2004 | Rosen et al. | |
| 2005/0071196 A1 | 3/2005 | Del Pin | |
| 2006/0173679 A1 * | 8/2006 | DelMonego et al. | 704/235 |

FOREIGN PATENT DOCUMENTS

| | | |
|---|---|---|
| JP | 11-345276 | 12/1999 |
| JP | 2001-344346 | 12/2001 |
| JP | 2002-140503 | 5/2002 |
| JP | 2004-118098 | 4/2004 |
| JP | 2005-149083 | 6/2005 |
| WO | WO 99/42933 A1 | 8/1999 |
| WO | W02004057439 A2 | 7/2004 |
| WO | WO 2005/04572 A1 | 5/2005 |
| WO | WO 2005/045720 A1 | 5/2005 |

OTHER PUBLICATIONS

Office Action issued by the Japanese Patent Office in Japanese Patent Application No. 2008-537255 on Oct. 2, 2012.

Notice of Granting Patent Right for Invention dated Sep. 25, 2012, from corresponding Chinese Application No. 200680039718.5.

Thinkplan INC., "XML Creator Web interface developing tool which can share knowledge—Best solution for designing B2B, electronic applications and intra-company approval documents as you wish!", XML Press, vol. 6, Gijutsu-Hyohron Co., Ltd., May 25, 2002, vol. 6, pp. 154-157.

Office Action from Japanese Patent Application No. 2008-537255, mailed Sep. 13, 2011.

* cited by examiner

METHOD AND SYSTEM FOR PROCESSING DICTATED INFORMATION

Related Applications

This application is a national stage filing under 35 U.S.C. § 371 of international PCT application PCT/IB2006/053801, filed Oct. 16, 2006, and titled "Method and system for processing dictated information," which claims priority to European Application No. 05110063.4, filed Oct. 27, 2005, and titled "Method and system for processing dictated information," the entire contents of each of which are incorporated herein by reference.

This invention pertains in general to the field of document creation through speech recognition. More particularly the invention relates to a method and a system for processing dictated information into a dynamic form, thus increasing recognition accuracy (learning or adaptation) based on the dictated form, and even more particularly to link document contents to a general relational database.

Speech recognition systems are today becoming increasingly effective and are well used within a plurality of industries. Speech recognition (SR) is the process by which an acoustic signal received by a microphone is converted to a document, comprising a set of words, by a computer. These recognized words may then be used in a variety of applications for different purposes. The automatic speech recognition systems, which convert speech into text, result in cost-efficient report creation and high transcription productivity.

The fact that these reports are treasures of information, which is very difficult and error prone to retrieve, increases the need for processing the information in a way that makes it easy to collect beneficial information.

It is known that the main method of dictating a report is currently dictation of plain text. This requires the user to know the structure of the document he wants to dictate and use full, grammatically and semantically correct sentences. From a speech recognition point of view, plain text dictation is straight forward, yet certain improvements cannot be realized since the Speech recognition (SR) engine cannot make any interference reliably as to the structure of the report.

Another method for dictation is form filling, which takes templates to an extreme. According to this method, most commonly used reports are transformed to a form, so that users know exactly what to dictate where. This also makes it easier to extract information from the report, since the report form is known to the user. While this is ok in "commonly used" reports, it either doesn't address less common cases, or it becomes so unwieldy to cover all possibilities that it is impractical.

From a speech recognition point of view, form filling dictation may improve the accuracy, since the context and grammars can be fine-tuned to individual fields. But this accuracy comes at the cost of development complexity, since the forms are usually determined at the customer site, which requires clever algorithms and/or easy-to-use tools to transform the form to a format that can be used by the SR engine and the SR application.

Several ideas of improving the method of dictating and processing the reports have been proposed over the last few years. One example has been disclosed in U.S. Pat. No. 6,813,603 which discloses a system and a method for user controlled insertion of standardized text in user selected fields while dictating text entries for completing a form.

It is also known that the information in a commonly used report, such as a medical report, is heavily formatted and has little or no structure for automatic processing, which makes it very difficult to collect information from completed reports that might be beneficial, such as prescribed medications, number of diagnosis of a certain condition etc. The completed report is also billed (coded) according to its content, which also is very difficult to achieve through parsing the report alone.

One problem is that recognized text is not easy to process. For this purpose there are expensive and error-prone tools such as coding tools, but these are not optimal. Another problem is the structure of the reports. Guidelines for dictating reports are usually determined centrally and the authors do not always hold to these guidelines when dictating. Additionally, each author has his/her own dictation style. Usually authors use the same report structure and even the same phrases. Some authors dictate the same things over and over again. They may also forget to dictate or address some points that are required.

In the field of health care there are also privacy concerns since the documents, medical reports, are full of private health information which needs to be protected, both ethically and legally.

Hence, an improved method for processing dictated information would be advantageous.

Accordingly, the present invention preferably seeks to mitigate, alleviate or eliminate one or more of the above-identified deficiencies in the art and disadvantages singly or in any combination and solves at least one of the above mentioned problems, at least partly, by providing a method and a system that makes it possible to process dictated information into a dynamic form and links the dictated information in the dynamic form to an external database, according to the appended patent claims.

The invention enables providing a method for creating a document report where all relevant data is marked and linked to an external database. The system according to the invention offers a report template which contains building blocks that are automatically created by a voice macro. The voice macro defines work-type fields that are to be filled by an author, so that the author doesn't forget what to dictate or to fill into the fields since he/she can see them. Relevant building blocks of such a report are automatically inserted, for instance, once the author indicates that he/she wants to dictate a chest x-ray of a patient. These blocks also contain markers that may be used to create distinct nodes in a document once the document is finished. The nodes are created by a general markup language, such as the Extended Markup Language (xml). In this way, specific parts of the document may be unmistakably mapped to an external database, whereby no parsing or coding is needed.

According to one aspect of the invention, a method for processing dictated information into a dynamic form is provided. The method comprises presenting an image, belonging to an image category, to a user. The method further comprises dictating a first section of speech associated with the image category, retrieving an electronic document having a previously defined document structure associated with the first section of speech, thus associating the document structure with the image, wherein the document structure comprises at least one text field, presenting at least a part of the electronic document having the document structure on a presenting unit, dictating a second section of speech and processing the second section of speech in a speech recognition engine into dictated text, and associating the dictated text with the text field.

According to another aspect of the invention, a system for processing dictated information into a dynamic form is provided. The system comprises means for presenting an image, belonging to an image category, to a user. The system further comprises means for dictating a first section of speech associated with the image category, retrieving an electronic document having a previously defined document structure associated with the first section of speech, thus associating the document structure with the image, wherein the document structure comprises at least one text field. Moreover, the system comprises a presenting unit for presenting at least a part of the electronic document having the document structure, means for dictating a second section of speech, a speech recognition engine for processing the said second section of speech into dictated text and means for associating the dictated text with the text field.

The present invention has for instance the advantage over the prior art that in a document, created through SR, all relevant data can be marked and linked to an external database.

In addition, the same approach may also decouple the order and structure of the document sections from the content. The author may dictate in any order he likes, using alternative key words if he wishes, and the final document may still look uniform.

These and other aspects, features and advantages of which the invention is capable of will be apparent and elucidated from the following description of embodiments of the present invention, reference being made to the accompanying drawing, in which FIG. 1 is a schematic diagram in the form of a flowchart showing a dictation chain according to the invention.

The following description focuses on an example of the present invention applicable to processing dictated information in a medical case, i.e. in the non-limiting example an MRI (magnetic resonance imaging)-examination, into a dynamic form and more particularly to link the dictated information in the dynamic form to an external database. However, it will be appreciated that the invention is not limited to this application but can be applied to many other chains of dictation, such as legal and insurance cases.

It will be understood that the figures are merely schematic. A dictation chain according to the invention is shown in FIG. 1. The chain starts with that an author 2, in this case a doctor, receives an image 3, in this case an image created by an MRI (magnetic resonance imaging) modality during an MRI-examination, for instance of the head of a patient. The image may also be derived from other medical image modalities, such as Computer Tomography (CT) or Ultrasound machines. The doctor studies this image, for instance on a display of a medical workstation. Then, the doctor dictates a voice macro "MRI-report" which is sent to a template database (not shown). The voice macro is for instance recorded as an acoustic signal received via a microphone in a SR engine and an SR application run on the medical workstation, or another computer, which for instance is distributed in a network, which is accessible to the doctor for dictation. The acoustic signal is treated by the SR engine and is converted to a computer command corresponding to the acoustic voice macro. In this example, the voice macro indicates that a report template 4 for MRI examination shall be used. The template 4 is requested from a template database (not shown). The report template 4 is then retrieved and received from the template database and presented on a screen 5, for instance the screen of the above-mentioned medical workstation. When the template 4 for MRI examination is displayed on screen 5, the doctor dictates relevant information such as plain text or other voice macros into the report template 4. During dictation, the dictated information is continuously sent to a speech recognition engine 6 where it is processed.

The speech recognition engine 6 may also be used for the above-mentioned SR of the voice macro. The finalized report 7 and the associated image 3 is linked to each other and stored in a database 8, which then may be committed to a electronic patient record (EPR), for instance as part of a Hospital Information System (HIS).

Now an illustrative example for the above-described process is given. The resulting text in the report template may be as follows:

Clinical Statement: [dictate clinical statement here]
History: The study was compared to a prior study dated [dictate previous study date here]
Findings: [dictate medical findings here]
Impression: [dictate impression gained from the study]
Medication: [list prescribed medication]

The bold text is entered automatically from the template 4, and the italic texts, between the brackets, are work-type fields to be filled by the doctor by dictation.

In general, the SR engine uses the whole radiology context (several tens of thousands of words and associated statistical models) for recognition in each field. The recognition accuracy of a computer system is higher, the more specific the text being dictated is. This is also true for a human listener, but since this is done without any effort, it is not noticeably. As an example, if a person is talking about a baseball game he has been to last weekend, he is not likely to use words such as "mammography" or "fibrocystic". But he can switch the topic eventually and still it is possible to follow what he is saying, especially if it is known that he is a doctor and is talking about some rare condition that he has identified.

In a method, e.g. implemented in software, this problem is addressed through targeted adaptation ConTexts. A ConText can be defined as a set of data that is specific to a topic, i.e. radiology, and contains a population of words (specialized lexicons and statistical language models) that are most likely to be found in a radiology report, and a complex statistical model of likelihood how these words can be used. A so-called SubConText (a subset of large lexicon and statistical language models) may also be created. These SubContexts may be switched accurately and quickly on the fly, depending on the place in the report. This is automatic in a report according to the embodiment of the invention whose building blocks have predefined work-type fields. For instance, if the field is called "measurements:" it is most likely that digits, numbers, units and type of measurement terms is dictated. The ConText is optimized and the recognition rate is increased significantly. Since the software knows what the doctor is dictating in this particular field, it doesn't have to use complex guessing algorithms. In some fields where the ConText is even more limited, e.g. date fields, the SR engine can switch to the SubConText or grammar for this field and the SR accuracy will rise drastically.

The work type fields, which are defined by voice macros, contains markers that may be used to create distinct nodes in an xml document, once the report is finished, so that no parsing is required. In this way, the specific parts may be unmistakably mapped to an external database, including but not limited to electronic patient records. The dictated text contained in a medication work type field is for instance:

Medication: [
Medication A
Medication B
Medication C ]

This information is exported as text to a specified xml code and the markers become nodes in this code. Such that the information in the medication field becomes:

```
<?xml version="1.0" encoding="ISO-8859-1" ?>
<!--
Copyright (c) 2005 Philips Austria GmbH, PSP
-->
<ORM_O01 xmlns:assume="assumptions for translation"
  assume:version="v23">
<ORM_O01.PIDPD1NTEPV1PV2IN1IN2IN3GT1AL1>
<MID>
<MID.1> Medication A <\MID.1>
<MID.2> Medication B <\MID.1>
<MID.3> Medication C <\MID.1>
<\MID>
...
```

In addition, the same approach may also decouple the order and structure of the document sections from the content. The doctors may dictate in any order they like, using alternative key words if they wish, and the end document may still look uniform. Since the fields are identified explicitly in the SR application, in a post-processing step, the order of the dictation may be changed, e.g. the doctor dictates a comparison date first, then his findings, whereupon he realizes that he forgot a clinical statement and dictates that clinical statement.

In another embodiment the voice macros are defined such that they may be executed in any order possible. In this way the doctor may dictate in any order he/she likes but during delivery an external tool will re-sort the fields and reformat them to be in a desired order and format, for instance previously defined by e.g. the hospital. The following example shows how the report may look like at every step of the method.

In the first step the doctor dictates the voice macro "Insert history" then the doctor dictates "twenty oh nine two thousand and four"
The report looks like:
History: Comparison was made to a previous study dated [20.09.2004]
Further on the doctor dictates the voice macro "Insert Findings" and the report looks like:
History: Comparison was made to a previous study dated [20.09.2004]
Findings:[ . . . ]
The doctor then dictates the findings and the report looks like:
History: Comparison was made to a previous study dated [20.09.2004]
Findings:[There is a focal area of heterogeneous of soft tissue . . . ]
Then he wants to dictate his clinical statement and dictates the voice macro "Insert clinical statement" and his statement and the report looks like:
History: Comparison was made to a previous study dated [20.09.2004]
Findings:[There is a focal area of heterogeneous of soft tissue . . . ]
Clinical statement:[pain above the right chest]
He dictates another voice macro "Insert impression" and the report looks like:
History: Comparison was made to a previous study dated [20.09.2004]
Findings:[There is a focal area of heterogeneous of soft tissue . . . ]
Clinical statement:[pain above the right chest]
Impression:[ . . . ]
He completes the impression field by dictating "category four mammo" and the report looks like:
History: Comparison was made to a previous study dated [20.09.2004]
Findings:[There is a focal area of heterogeneous of soft tissue . . . ]
Clinical statement:[pain above the right chest]
Impression:[category 4—suspicious abnormality. Biopsy should be considered. Correlation with physical examination findings is recommended . . . ]
Now, in a post processing step, the part about clinical statement can easily be moved to the beginning, where it makes more sense. The report becomes as follows:
Clinical statement:[pain above the right chest]
History: Comparison was made to a previous study dated [20.09.2004]
Findings:[There is a focal area of heterogeneous of soft tissue . . . ]
Impression:[category 4—suspicious abnormality. Biopsy should be considered. Correlation with physical examination findings is recommended . . . ]
This is a minor example, the building blocks of the text may be sorted in any way that is desired.

In another example of the invention one may expand or reduce the work type fields dynamically so that the complexity of the report form seen by the user is managed "as simple as possible, but not simpler".

The doctor receives for example a mammography image with a request to perform a mammography exam. The doctor executes a voice macro "mammography exam" and the screen fills with all the hints required to dictate such a report. Such as:
Clinical statement: [ . . . ]
History: [ . . . ]
Measurements: [ . . . ]
Findings: [ . . . ]
Assume that the findings is a possible benign finding. The doctor executes a voice macro "category O mammo" which results in an insert of a predefined text into the report:
Findings: [Category 0 mammogram—Need additional imaging evaluation.
Note: Further correlation by means of a physical exam is recommended since some cancers may be obscured by dense fibrocystic changes and occasionally can be missed on fatty infiltrated breasts.
Medication: [
(some medication name A)
(some medication name B)
etc
]
]
The report is automatically expanded with additional information related to the benign findings. In this way the doctor automatically knows what to look for and what medications are usually prescribed in this case. Similarly, depending on a condition, some fields may be removed from the report.

Applications and use of the above described system and method according to the invention are various and include exemplary fields such as any other medical specialty (including cardiology, oncology, emergency medicine etc.) but also legal fields, insurance and any other fields where documents are created from dictated speech (also through mobile devices such as PDAs or voice recorders, since they can also be fed to the recognition engine).

Although the present invention has been described above with reference to specific examples, it is not intended to be limited to the specific form set forth herein. Rather, the invention is limited only by the accompanying claims and, other examples than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for processing dictated information into a dynamic form, the method comprising:
   retrieving an electronic document having a document structure, wherein the document structure comprises at least one text field;
   presenting at least a part of the electronic document to a user;
   receiving speech input of first dictated information;
   processing the speech input in a speech recognition engine into dictated text;
   associating the dictated text with a first text field; and
   based at least in part on the speech input, adjusting a display of the electronic document to control how much of the electronic document is displayed to the user.

2. The method according to claim 1, wherein the electronic document having the document structure comprises is associated with a set of data that is specific to a topic and contains a population of words that are likely to be found in the at least one text field, and
   wherein processing the speech input in a speech recognition engine into dictated text comprises using a statistical model of likelihood of use of the population of words.

3. The method according to claim 2, wherein at least a portion of the set of data associated with the electronic document is associated with a specific text field in the document structure.

4. The method of claim 3, wherein the set of data comprises a first subset of data and a second subset of data, the first subset of data being associated with at least one first text field of the at least one text field of the electronic document and the second subset of data being associated with at least one second text field of the at least one text field, and
   wherein the method further comprises switching between the first subset of data and the second subset of data depending on a current text field selected by the user for dictation of text into the electronic document.

5. The method according to claim 1, wherein the document structure comprises a plurality of text fields, and the method further comprises:
   defining a voice macro associated with a specific text field of the text fields, such that the specific text field is chosen for receipt of the dictated text of the speech input when the voice macro is dictated by the user.

6. The method according to claim 5, further comprising:
   filling the plurality of text fields based on an order in which voice macros corresponding to each of the plurality of text fields are dictated by the user.

7. The method according to claim 1, wherein adjusting the display of the electronic document comprises dynamically expanding or reducing a number of text fields, of the at least one text field of the electronic document, presented to the user.

8. The method of claim 1, further comprising:
   displaying an image to the user;
   receiving, via a speech interface, a first speech input from the user regarding the image; and
   based at least in part on the first speech input, selecting, from at least one available electronic document, the electronic document to be retrieved and displayed.

9. The method according to claim 8, further comprising:
   linking the image to the electronic document having the document structure and the dictated text, and
   storing the image and the electronic document in a data store.

10. The method according to claim 9, further comprising:
    identifying the text field with a marker;
    converting the marked text field into a code string;
    storing the code string together with the image in the data store.

11. The method according to claim 10, wherein identifying the text field with the marker comprises automatically performing the identifying of the text field with the marker.

12. The method according to claim 10, wherein the converting the marked text field to a code string comprises exporting the marked text field as text and converting the markers into nodes, created by a general markup language, in a document having the document structure.

13. The method of claim 8, wherein:
    the image belongs to an image category,
    receiving the first speech input comprises receiving an indication of the image category, and
    selecting the electronic document based at least in part on the first speech input comprises selecting the electronic document associated with the image category.

14. A system for processing dictated information into a dynamic form, the system comprising:
    at least one processor programmed to perform acts of:
        retrieving an electronic document having a document structure, wherein the document structure comprises at least one text field;
    presenting at least a part of the electronic document having the document structure;
    receiving speech input of first dictated information;
    using a speech recognition engine, processing the speech input into dictated text;
    associating the dictated text with a first text field; and
    based at least in part on the speech input, adjusting a display of the electronic document to control how much of the electronic document is displayed to the user.

15. The system of claim 14, wherein the at least one processor is further programmed to perform acts of:
    displaying an image to the user;
    receiving, via a speech interface, a first speech input from the user regarding the image; and
    based at least in part on the first speech input, selecting, from at least one available electronic document, the electronic document to be retrieved and displayed.

16. The system of claim 15, wherein:
    the image belongs to an image category,
    receiving the first speech input comprises receiving an indication of the image category, and
    selecting the electronic document based at least in part on the first speech input comprises selecting the electronic document associated with the image category.

17. The system of claim 15, wherein the at least one processor is further programmed to perform acts of:
- linking the image to the electronic document having the document structure and the dictated text; and
- storing the image and the electronic document in a data store.

18. The system of claim 14, wherein adjusting the display of the electronic document comprises dynamically expanding or reducing a number of text fields, of the at least one text field of the electronic document, presented to the user.

19. At least one non-transitory computer-readable storage medium having encoded thereon a computer program that, when executed by a computer, causes the computer to perform a method for processing dictated information into a dynamic form, the method comprising:
- retrieving an electronic document having a document structure, wherein the document structure comprises at least one text field;
- presenting at least a part of the electronic document to a user;
- processing speech input in a speech recognition engine into dictated text;
- associating the dictated text with a first text field; and
- based at least in part on the speech input, adjusting a display of the electronic document to control how much of the electronic document is displayed to the user.

20. The at least one non-transitory computer-readable storage medium of claim 19, wherein the method further comprises:
- displaying an image to the user;
- receiving, via a speech interface, a first speech input from the user regarding the image; and
- based at least in part on the first speech input, selecting, from at least one available electronic document, the electronic document to be retrieved and displayed.

21. The at least one non-transitory computer-readable storage medium of claim 20, wherein:
- the image belongs to an image category,
- receiving the first speech input comprises receiving an indication of the image category, and
- selecting the electronic document based at least in part on the first speech input comprises selecting the electronic document associated with the image category.

22. The at least one non-transitory computer-readable storage medium of claim 20, wherein the method further comprises:
- linking the image to the electronic document having the document structure and the dictated text; and
- storing the image and the electronic document in a data store.

23. The at least one non-transitory computer-readable storage medium of claim 19, wherein adjusting the display of the electronic document comprises dynamically expanding or reducing a number of text fields, of the at least one text field of the electronic document, presented to the user.

* * * * *